United States Patent [19]

Christidis et al.

[11] Patent Number: 4,960,923
[45] Date of Patent: Oct. 2, 1990

[54] PURE CRYSTALLINE METHYL 2-ACRYLOYLAMINO-2-METHOXY ACETATE AND A PROCESS FOR PREPARING IT

[75] Inventors: Yani Christidis, Paris; Christian Sidot, Ezanville, both of France

[73] Assignee: Societe Francaise Hoechst, Puteaux, France

[21] Appl. No.: 266,485

[22] Filed: Nov. 2, 1988

[30] Foreign Application Priority Data
Nov. 4, 1987 [FR] France ................................ 87 15291

[51] Int. Cl.$^5$ ............................................ C07C 103/66
[52] U.S. Cl. ........................................................ 560/170
[58] Field of Search ........................................ 560/170

[56] References Cited

U.S. PATENT DOCUMENTS 4,443,623  4/1984  Photis .................................... 560/170
4,760,168  7/1988  Schirmann ........................... 560/170

FOREIGN PATENT DOCUMENTS 0138025  4/1985  European Pat. Off. .

*Primary Examiner*—Michael L. Shippen
*Attorney, Agent, or Firm*—Browdy and Neimark

[57] ABSTRACT

The process for preparing a novel product, pure crystalline methyl 2-acryloylamino-2-methoxyacetate, involves reacting pure crystalline, anhydrous acrylamidoglycolic acid in an anhydrous medium with methanol in the presence of hydrogen chloride. This is subsequently neutralized with an alkali metal bicarbonate, and then the mineral salts are filtered off. Finally, pure crystalline methyl 2-acryloylamino-2-methoxyacetate is obtained by taking up the concentrated reaction medium in 1,1,1-trichloroethane under vacuum.

2 Claims, No Drawings

PURE CRYSTALLINE METHYL 2-ACRYLOYLAMINO-2-METHOXY ACETATE AND A PROCESS FOR PREPARING IT

BACKGROUND OF THE INVENTION

1. Field of the invention

The present invention concerns pure crystalline methyl 2-acryloylamino-2-methoxy acetate and a process for preparing it.

Methyl 2-acryloylamino-2-methoxy acetate, hereinafter termed MAGME, is a known multifunctional monomer which is currently used as a reticulant monomer.

The following methods have been proposed for its preparation:

Etherification with methanol in an acid medium of methyl acrylamidoglycolate, the latter being the product of condensation of acrylamide with methyl 2-hydroxy-2-methoxyacetate (Canadian patent 1 209 583).

Simultaneous etherification and esterification using methanol in an acid medium of acrylamidoglycolic acid crystallized with one molecule of water (European patent No. 0 020 000 and U.S. Pat. No. 4,656,308).

These methods, however, result in crude MAGME containing a number of impurities, in particular acrylamide, which cause problems in their subsequent use in some applications.

It has now, surprisingly, been discovered that a novel, simple process for the preparation of MAGME produces a good yield of a pure, crystalline product.

SUMMARY OF THE INVENTION

The process is characterized in that pure, crystalline anhydrous acrylamidoglycolic acid (hereinafter termed AAG) is reacted with methanol in an anhydrous medium in the presence of hydrogen chloride, the reaction medium is subsequently neutralized with an alkali metal bicarbonate, the mineral salts are then filtered off and finally pure crystalline MAGME is isolated by taking up the reaction medium in 1,1,1-trichloroethane under vacuum.

The following conditions preferably apply in carrying out the inventive process:
- all the steps in the process are carried out at a temperature which is lower than 35° C.;
- 1 mole pure crystalline anhydrous AAG is reacted with more than 10 moles methanol in the presence of 1 mole anhydrous hydrogen chloride at a temperature between 30° and 35° C.;
- the reaction medium is neutralized with sodium bicarbonate;
- at the end of the reaction, excess methanol and the water which is formed are eliminated by initial vacuum distillation at a temperature below 35° C., then by azeotropic distillation under vacuum with 1,1,1-trichloroethane at a temperature below 35° C.;
- if necessary, the MAGME is recrystallized from 1,1,1-trichloroethane.

Pure crystalline anhydrous acrylamidoglycolic acid used as the starting material may be obtained using the process described in French patent application No. 87 03545 of 16 March 1987. As there stated, pure anhydrous crystallized acrylamidoglycolic acid is obtained by reacting acrylamide with glyoxylic acid in an aqueous solution at a concentration equal to or higher than 60% and at a temperature of between 35° C. and 80° C., the reaction being carried out at a pH of less than 7 in the absence of a catalyst of any type whatsoever.

MAGME obtained from the process according to the present invention is crystalline and colorless, with a sharp melting point of 76° C. and an index of double bond which agrees with theory. In addition, product analyses using either microanalysis, high performance liquid chromatography, differential thermal analysis or proton NMR at 200 MHz in deuterated chloroform cannot detect any impurities. The product is therefore highly stable and is particularly appropriate for use in known applications.

EXAMPLES

The following examples are intended to illustrate the invention without in any way limiting its scope.

EXAMPLE 1

290 g (2 moles) pure crystalline anhydrous AAG obtained using the method of Example 1 in French patent application No. 87 03545 mentioned above and 3.2 g paramethoxyphenol were dissolved at room temperature in 897 g (28 moles) anhydrous methanol.

The solution was maintained at 30°–35° C. by slight external cooling and 73 g (2 moles) anhydrous hydrogen chloride was introduced over a one hour period, with stirring. The solution was then left for two hours with stirring at 30° C. before slowly neutralizing it with 185 g (2.2 moles) sodium bicarbonate. After stirring for 30 minutes, the mineral salts were eliminated by filtering and the filtrate was concentrated under a vacuum of about 13 mbar at a temperature below 30° C. 530 g of a methanol-water mixture was thus recovered. The reaction solvents were subsequently eliminated by introducing 1 350 g 1,1,1-trichloroethane into the reaction medium then azeotropically distilling under vacuum (13 mbar) at a temperature below 35° C. by continuous introduction of fresh 1,1,1-trichloroethane at a rate approximately equal to that of distillate formation.

After introducing 1 350 g 1,1,1-trichloroethane the distillation was halted and the reaction medium cooled. The desired product crystallized out spontaneously. It was filtered and dried to constant weight under vacuum at 30° C.

267 g (1.54 mole) crystalline, colorless MAGME was obtained. It had a melting point of 76° C. and a yield of 77% of theory calculated with respect to the

| Microanalysis | C % | H % | N % | O % |
| --- | --- | --- | --- | --- |
| $C_7H_{11}NO_4$ calculated | 48.55 | 6.4 | 8.09 | 36.96 |
| M. Wt = 173.2 found | 48.6 | 6.5 | 8.1 | |

Double bond quantitative determination: 5.72±0.04 mequivalents g, i.e. 99±1% of theory.
Water content: less than 0.1%.
High performance liquid chromatography: one single peak representing 99.5% MAGME.
Differential thermal analysis: melting pt=76° C.
Infrared/physical analysis: spectrum agreed with structure.
Proton NMR, 200 MHz, physical analysis in deuterated chloroform:
6.82 ppm, d, 1H, J=9 Hz, NH,
6.65 ppm, d, 1H, J=9 Hz, CH—N,
6.40 ppm,dd, 1H, J=17 Hz and J=1.5 Hz, $H_2C=$,
6.20 ppm,dd, 1H, J=17 Hz and J=10 Hz, CH—CO,
5.78 ppm,dd, 1H, J=10 Hz and J=1.5 Hz, $H_2C=$, 3.83 ppm, s, 3H, COOC$\underline{H}_3$,
3.48 ppm, s, 3H, OC$\underline{H}_3$.

EXAMPLE 2

The method of Example 1 was followed, replacing pure crystalline anhydrous acrylamidoglycolic acid by an equivalent quantity of acrylamidoglycolic acid crystallized with one molecule of water.

259 g (1.5 mole) crystalline, colorless MAGME was obtained, having a melting point of 73° C. (standard 76° C.).

Double bond quantitative determination: 5.6±0.04 mequivalents/g i.e. 97±1% of theory. p0 High performance liquid chromatography:

96% MAGME,
2% 2-acryloylamino-2-methoxyacetic acid,
1.8% methyl 2-acryloylamino-2-hydroxy acetate,
0.2% methyl bisacrylamidoacetate.

This product could not be purified by recrystallization from 1,1,1-trichloroethane. Thus the inventive process applied to acrylamidoglycolic acid crystallized with one molecule of water produces only 96% pure MAGME with a yield of 75% of theory.

COMPARATIVE EXAMPLE

The process described in Example 1 of European patent No. 0 020 000 was carefully followed. 264 g crude MAGME was obtained, which had an unclear melting point of 66±2° C.

High performance liquid chromatography showed the following:

80% MAGME,
4% methyl 2-acryloylamino-2-hydroxyacetate,
1.7% water (Karl Fisher determination),
1.5% acrylamide,
0.2% AAG,
0.5% 2-acryloylamino-2-methyoxyacetic acid,
0.1% glyoxylic acid,
12% unidentified impurities.

The product could not be purified by either distillation or recrystallization. The yield was 83% of theory calculated with respect to the amount of AAG used; the product was 80% pure.

The description and examples of the present invention are for illustrative purposes only and are, of course, not limiting. Any beneficial modification may be made thereto without departing from the scope of the invention.

There is claimed:

1. A process for the preparation of pure crystalline methyl 2-acryloylamino-2-methoxyacetate by reacting pure crystalline anhydrous acrylamidoglycolic acid in an anhydrous medium with methanol in the presence of hydrogen chloride, subsequently neutralizing the reaction medium with an alkaline metal bicarbonate, then filtering off the mineral salts, and finally isolating said pure crystalline methyl 2-acryloylamino-2-methoxyacetate by distillation with 1,1,1-tricholoroethane under vacuum and crystallization in 1,1,1-trichloroethane.

2. A process according to claim 1 wherein one mole pure crystalline anhydrous acrylamidoglycolic acid is reacted in an anhydrous medium at a temperature of between 30° and 35° C. with more than 10 moles methanol in the presence of one mole anhydrous hydrogen chloride, the reaction medium is then neutralized using sodium bicarbonate and the mineral salts are filtered off, the excess methanol and water formed is eliminated by initial vacuum distillation at a temperature below 35° C. then by azeotropic distillation under vacuum with 1,1,1-trichloroethane at a temperature below 35° C.

* * * * *